United States Patent [19]
Tsuchiya et al.

[11] Patent Number: 5,807,676
[45] Date of Patent: Sep. 15, 1998

[54] VARIETY CLASSIFICATION METHOD FOR BARLEY OR MALT USING GENE DIAGNOSIS AND THE PRIMER USED THEREFOR

[75] Inventors: Youichi Tsuchiya; Shigeki Araki, both of Yaizu, Japan

[73] Assignee: Sapporo Breweries Limited, Tokyo, Japan

[21] Appl. No.: 534,684

[22] Filed: Sep. 27, 1995

[30] Foreign Application Priority Data

Sep. 29, 1994 [JP] Japan .................................. 6-261286

[51] Int. Cl.$^6$ .............................. C12Q 1/68; C12P 19/34; C07H 21/04; C12N 15/00
[52] U.S. Cl. ........................... 435/6; 435/91.1; 435/91.2; 536/23.1; 536/24.3; 536/24.33; 800/235; 935/76; 935/77; 935/78
[58] Field of Search ............................. 435/6, 91.1, 91.2, 435/270, 183; 536/23.1, 24.3–24.33; 935/8, 76, 77, 78; 800/235

[56] References Cited

PUBLICATIONS

Yoshigi et al., "PCR Cloning and Sequencing of the beta–Amylase cDNA from Barley," J. Biochem. 115, 47–51, Jan. 1994.
Forde, B.G., et al., Nucleic Acids Research vol. 13, No. 20: 7327–7339, 1985.
S. Weining et al., Theo. Appl. Genet. 82: 209–216, 1991.
N. Yoshigi et al., J. Biochem. 115: 47–51, 1994.
R.J. Rahmatullah et al., Plant Mol. Biol. 12: 119–121, 1989.
J.C. Litts et al., Eur. J. Biochem. 194: 831–838, 1990.
P.W. Chee et al. "Development of Polymerase Chain Reaction for Barley Genome Analysis", Journal Am.Soc.Brewing Chemists, (1993), vol. 1, No. 3, pp. 93–96.

*Primary Examiner*—Bradley L. Sisson
*Attorney, Agent, or Firm*—Bell, Boyd & Lloyd

[57] ABSTRACT

The variety of barley or malt is quickly and conveniently classified by amplifying the genomic DNA by PCR with the primer consisting of the sequence complementary to the gene that is important for brewing and examining the difference in the base sequence of said DNA.

4 Claims, 2 Drawing Sheets

VARIETY TYPE
M A B

VARIETY TYPE

Hae III

M A B C D E M A B C D E

VARIETY CLASSIFICATION METHOD FOR BARLEY OR MALT USING GENE DIAGNOSIS AND THE PRIMER USED THEREFOR

FIELD OF THE INVENTION

The present invention relates to a method for classifying the variety of malting barley or malt using gene diagnosis and primers used for said method.

DESCRIPTION OF THE RELATED ART

For variety classification of barley and malt, there has been conventionally used a method for classifying the variety by comparing an SDS polyacrylamide gel electrophoretic pattern of hordein and esterase contained therein. In addition, a classification method using gene diagnosis has recently been developed (e.g., Chee et al., J. Am. Soc. Brew. Chem., 51, 93 (1993)).

However, the variety classification method by way of comparing the electrophoretic pattern of hordein and esterase is not necessarily an accurate classification method, because the electrophoretic pattern may be modified according to growing conditions of barley or due to the degradation of the hordein and esterase by protease during malting process. Furthermore, since most classification methods using gene diagnosis use genes from unidentified origin as probe or primer, there has been a problem that results obtained by the method cannot be directly correlated with the effect on the quality of brew, even though mutation of materials or contamination of materials with other varieties are indicated.

The present invention has been made considering the problem described above, and aims to provide a more satisfactory method for classifying barley or malt using gene diagnosis from the viewpoint of breeding malting barley or quality control of brewing materials.

SUMMARY OF THE INVENTION

In view of the situations described above, through continual ardent studies, the present inventors identified the site wherein the base sequence differs among varieties in the gene which is important for brewing, and accomplished the present invention.

That is, the present invention provides a variety classification method for barley or malt by performing polymerase chain reaction (PCR) with a set of primers designed to flank the site of the gene which is important for brewing, wherein the base sequence of the gene is made different among varieties so as to amplify the genomic DNA of barley or malt, and classifying the variety of barley or malt based on the difference in base sequence of the amplified DNA.

TABLE 1

| Targeted gene | Primer sequence | |
|---|---|---|
| β-Amylase | SEQ ID no 1 (1) | 5'-TTCAAAGCAGCAGCAGCG-3' |
| | SEQ ID no 2 (2) | 5'-TTCTTCTGGTGCGCTCATC-3' |
| α-Amylase | SEQ ID no 3 (3) | 5'-ATAAGTGGGCATCAATTCGGC-3' |
| | SEQ ID no 4 (4) | 5'-GTGTGTCTGGCCAGGTAT-3' |
| β-Glucanase | SEQ ID no 5 (5) | 5'-CGTGAAAAAACCGCCGCCGA-3' |
| | SEQ ID no 6 (6) | 5'-CTTTCTCTCTCTAGCTGCGT-3' |
| B1-Hordein | SEQ ID no 7 (7) | 5'-CCACCATGAAGACCTTCCTC-3' |
| | SEQ ID no 8 (8) | 5'-TCGCAGGATCCTGTACAACG-3' |

The present invention also provides primers used for the variety classification method. Primers according to the present invention can be synthesized with a commercial automated DNA synthesizer using the β-cyanoethylphosphoamidide method or thiophosphite method.

More precisely, the present invention provides a variety classification method for barley or malt comprising amplification of the genomic DNA of barley or malt by PCR with the primer having the base sequence complementary to the gene which is important gene in the brewing, and examination of the difference of base sequence of the amplified DNA.

The present invention also provides a variety classification method for barley or malt comprising the amplification of genomic DNA of barley or malt by PCR, which is performed with either a set of oligonucleotides consisting of the sequence of (1) 5'-TTCAAAGCAGCAGCAGCG-3' (SEQ ID NO: 1) and (2) 5'-TTCTTCTGGTGCGCTCATC-3' (SEQ ID NO: 2) or a set of oligonucleotides composed of the sequence complementary to the nucleotides as the essential primer, and also a set of oligonucleotides consisting of the sequence of (3) 5'-ATAAGTGGCCATCAATTCGGC-3' (SEQ ID NO: 3) and (4) 5'-GTGTGTCTGGCCAGGTAT-3' (SEQ ID NO: 4) or a set of oligonucleotides composed of the sequence complementary to them as the selective essential primer, and using either one of the two sets of essential primers and either one of the two sets of selective essential primers or either one primer thereof, and the classification based on the difference in the base sequence of said DNA.

Furthermore, the present invention provides a variety classification method for barley or malt comprising the amplification of the genomic DNA of barley or malt by PCR, which is performed with oligonucleotides consisting of the sequence of (5) 5'-CGTGAAAAAACCGCCGCCGA-3' (SEQ ID NO: 5), (6) 5'-CTTTCTCTCTCTAGCTGCGT-3' (SEQ ID NO: 6), (7) 5'-CCACCATGAAGACCTTCCTC-3' (SEQ ID NO: 7) and (8) 5'-TCGCAGGATCCTGTACAACG-3' (SEQ ID NO: 8) or oligonucleotide composed of the sequence complementary to them as a group of selective primers and further using, in addition to the essential primers and the selective essential primers, combination of at least any one or any two primers from the group of selective primers, and the classification of a variety of barley or malt based on the difference in the base sequence of the amplified DNA.

Furthermore, the present invention provides PCR primers comprising oligonucleotides consisting of the sequences 1–6 shown in the sequence listing table, or those consisting of sequences complementary to them.

According to the present invention, the genomic DNA is first extracted from the sample of barley or malt. Extraction of the genomic DNA may be carried out, for example, by a CTAB method (Nucleic Acids Res., 8, 4321 (1980)). Then, a portion of the targeted gene is amplified by applying the primer of the present invention to the genomic DNA. The partial amplification of the genomic DNA may be carried out, for example, by PCR (Science, 230, 1350 (1985)). Then, the variety of barley or malt is classified either by the base sequence determination of amplified DNA thus obtained or based on the difference in the base sequence detected by electrophoresis on denatured gradient gel or temperature gradient gel, or on the restriction enzyme cleavage pattern.

Since the method of the present invention aims to target the gene which is important for brewing, it is highly possible that results obtained may directly influence the quality of brew. Therefore, the method may become a satisfactory variety classification method from the viewpoint of breeding of brewer's barley or the quality control of brewing material.

DETAILED DESCRIPTION OF THE INVENTION

The invention will now be described with reference to specific examples, however, it should understood that the technical scope of the invention is not to be construed as being limited to them in any way.

EXAMPLE 1

Extraction of the Genomic DNA

In this embodiment, as the variety of barley or malt, Amagi Nijo (called Variety No. 1 hereinafter), Haruna Nijo (called Variety No. 2 hereinafter), Misato Golden (Variety No. 3 hereinafter), Clipper (called Variety No. 4 hereinafter), Schooner (called Variety No. 5 hereinafter), Stirling (called Variety No. 6 hereinafter), Harrington (called Variety No. 7 hereinafter), Manley (called Variety No. 8 hereinafter), Ellice (called Variety No. 9 hereinafter) and Alexis (called Variety No. 10 hereinafter) were used.

Embryos of barley or leaf buds of malt were taken out and the genomic DNA was extracted from them using "Plant Genome Extraction Kit" (Clontech).

EXAMPLE 2

Design and Synthesis of Primer

Various primers were designed from known base sequences of the barley genes important for brewing, including those of β-amylase, SEQ ID NO:9 (J. Biochem., 115, 47 (1994)), α-amylase, SEQ ID NOS: 10–11 (Plant Mol. Biol., 12, 119 (1989)), β-glucanase, SEQ ID NO: 12 (Eur. J. Biochem., 194, 831 (1990)), and B1-hordein, SEQ ID NO: 13 (Nucleic Acid Res., 13, 7327 (1985)). PCR was performed with these primers, and DNAs thus amplified were examined for the difference in the base sequence among varieties using temperature gradient gel electrophoresis or based on the base sequence determination.

As a result, it became clear that, using the primer (1)–(8), the DNA region wherein the base sequence is different among varieties can be amplified, and utilizing the restriction enzyme site in that region, the variety classification of barley or malt may become possible. Synthesis and purification of primers were entrusted to Sawady Technology Co. Ltd.

EXAMPLE 3

Variety Classification Method Using Primer (1) and (2)

Figure 1:
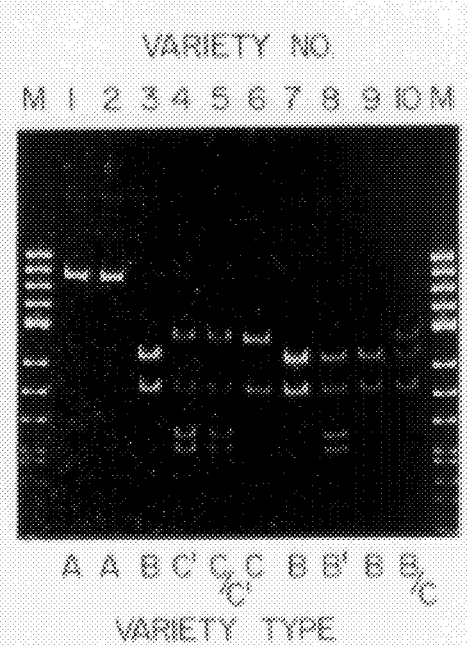
FIG. 1 is a photograph of the polyacrylamide gel electrophoretic pattern of DNAs which were amplified by PCR with primers (1) and (2), and then treated with restriction enzymes NcoI and EcoT22I. In the figure, 1–10 correspond to the variety of barley, A, B, B', C, and C' denote the type of electrophoretic pattern, and M is DNA MW marker 9 (Nippon Gene).

A PCR mixture (100 μl) which contained the genomic DNA (100 ng) extracted from 10 barley grains of each variety, dNTPs (20 nmol each), primers (1) and (2) (10 pmol each) and Taq DNA polymerase (2.5 U) was subjected to 33 cycles of reaction wherein each cycle consisted of incubating the mixture in sequence at 94° C. for 1 min, 55° C. for 2 min, and 72° C. for 1 min, and then finally treated at 72° C. for 5 min. After the completion of the PCR, restriction enzymes NcoI and EcoT22I (5 U each) and a buffer for the enzymatic reaction were added to the reaction mixture (8 μl), and the mixture was incubated at 37° C. for 1 h. This reaction mixture was electrophoresed on 5% polyacrylamide gel. After the electrophoresis, the gel was stained with ethidium bromide, and then the DNA were made visible by UV exposure. Results are shown in FIG. 1. As shown in this figure, from the electrophoretic pattern of the fragments of DNAs obtained by digestion with restriction enzymes NcoI and EcoT22I, 10 varieties of barley could be classified into 5 types (A, B, B', C and C'). Furthermore, based on results of analyses on single grains, Variety Nos 5 and 10 were found to be a mixed type consisting of either C and C' or B and C, therefore denoted as C/C' and B/C respectively.

EXAMPLE 4

Variety Classification Method Using Primers (3) and (4)

Figure 2:
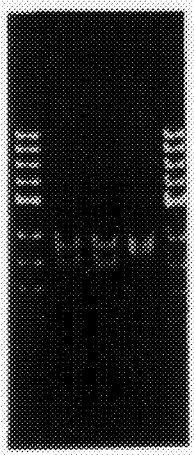
FIG. 2 is a photograph of the polyacrylamide gel electrophoretic pattern of DNAs which were amplified by PCR with primers (3) and (4), and then treated with restriction enzyme TaqI. In the figure, A, B and C denote the type of electrophoretic pattern and M is DNA MW marker 9 (Nippon Gene).

Analysis was performed under similar conditions to those described for Example 3, except that PCR was performed with the primer sequences (3) and (4) instead of (1) and (2) and subjected to 30 cycles instead of 33, and the restriction enzyme digestion was carried out with TaqI at 65° C. instead of NcoI and EcoT22I at 37° C. As a result, as shown in FIG. 2, the electrophoretic pattern could be classified into 3 types (A, B and C).

EXAMPLE 5

Variety Classification Method Using Primers (5) and (6)

Figure 3:
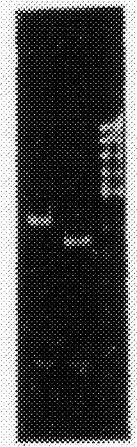
FIG. 3 is a photograph of polyacrylamide gel electrophoretic pattern of DNAs which were amplified by PCR with primers (5) and (6), and then treated with restriction enzyme HaeIII. In the figure, A and B denote the type of electrophoretic pattern and M is DNA MW marker 9 (Nippon Gene).

Analysis was performed under similar conditions to those described for Example 3, except that PCR was performed with the primer sequences (5) and (6) instead of (1) and (2) and subjected to 30 cycles instead of 33, and restriction enzyme digestion was carried out with HaeIII instead of NcoI and EcoT22I. As a result, as shown in FIG. 3, the electrophoretic pattern could be classified into 2 types (A and B).

EXAMPLE 6

Variety Classification Method Using Primers (7) and (8)

Figure 4:
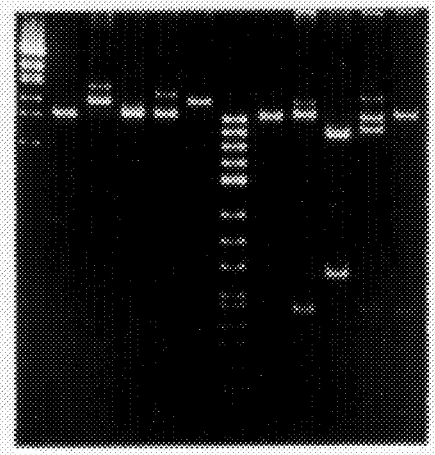
FIG. 4 is a photograph of polyacrylamide gel electrophoretic pattern of DNAs which are amplified by PCR with primers (7) and (8) (left half, A–E) and those which were then treated with restriction enzyme HaeIII (right half, A–E). In the figure, A, B, C, D and E denote the type of polyacrylamide gel electrophoretic pattern, and M is DNA MW marker 9 (Nippon Gene) and M' DNA MW marker 2 (Nippon Gene).

PCR was performed under similar conditions to those described for Example 3, except for using the primer sequences (7) and (8), subjected to 30 cycles instead of 33, and annealing at 57° C. instead of 55° C. A portion of the PCR products were electrophresed and the result was as shown on the left half of FIG. 4. Then, the PCR products were digested with the restriction enzyme HaeIII under similar conditions to those described for Example 3, and electrophoresed. The fragment patterns were as shown on the right half of FIG. 4. By comparing the results from intact and digested PCR products, as shown in FIG. 4, the electrophoresis pattern could be classified into 5 types (A, B, C, D and E).

EXAMPLE 7

Variety Classification Method By Overall Evaluation

Results of the type classification performed in Examples 3–6 are summarized in Table 2. These results show that it is possible to classify all of the 10 variesties by using the overall evaluation.

TABLE 2

| | | Type classification | | | | | | | | | | |
|---|---|---|---|---|---|---|---|---|---|---|---|---|
| | | | | | | Variety | | | | | | |
| PCR Primers | | 1 | 2 | 3 | 4 | 5 | 6 | 7 | 8 | 9 | 10 |
| (1), | (2) | A | A | B | C' | C/C' | C | B | B' | B | B/C |
| (3), | (4) | A | B | C | C | A | A | C | C | A | A |
| (5), | (6) | A | A | B | A | B | B | A | A | B | B |
| (7), | (8) | A | A | A/B | C | B | D | B | A | B | A/C/E |

EXAMPLE 8

Purity Test of Variety

Out of barley or malt purchased, 100 grains or 100 leaf buds as one sample lot were subjected to analysis of type classification described above in Examples 3–6. As a result, DNA fragments corresponding to the type of variety indicated at the time of purchase were identified, and the purity of variety could be determined by examining whether DNA fragments were contaminated with different type to those derived from other varieties.

When contamination with other varieties is expected, the purity of the sample can be estimated to a certain extent by quantifying the intensity of an electrophoretic band with an image analyzer. Furthermore, when each single grain or leaf bud is subjected to similar analysis, the extent of contamination and type of contaminating variety may be possibly determined qualitatively as well as quantitatively.

Since primers according to the present invention are prepared to target the gene which is important for brewing, it is highly possible that results obtained by this invention will directly affect the quality of brewing products. Therefore, using the variety classification method with such primers, a satisfactory variety classification can be carried out from the viewpoint of breeding of barley for brewing and the quality control of materials used for brewing.

---

What is claimed is:

1. A method for identifying a variety of barley or malt comprising:

a) amplifying genomic DNA of barley or malt with a primer combination selected from the group consisting of SEQ ID NO:1, SEQ ID NO:2, SEQ ID NO:3, SEQ ID NO:4, SEQ ID NO:5, and SEQ ID NO:6; and b) identifying said variety of barley or malt by evaluating differences in length, or base sequence, of the amplified DNA.

2. The method of claim 1 wherein the group of primers further consists of primers having the nucleotide sequence set forth in SEQ ID NO:7 and SEQ ID NO:8.

3. The method of claim 1 wherein the variety of barley or malt is selected from the group consisting of Amagi Nijo, Misato Golden, Clipper, Schooner, Stirling, Harrington, Manley, Ellice, and Alexis.

4. A PCR primer selected from the group consisting of SEQ ID NO:1, SEQ ID NO:2, SEQ ID NO:3, SEQ ID NO:4, SEQ ID NO:5, and SEQ ID NO:6.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

TTCAAAGCAG CAGCAGCG                                               1 8

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TTCTTCTGGT GCGCTCATC                                              1 9

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
ATAAGTGGGC ATCAATTCGG C                                              21
```

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
GTGTGTCTGG CCAGGTAT                                                  18
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
CGTGAAAAAA CCGCCGCCGA                                                20
```

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
CTTTCTCTCT CTAGCTGCGT                                                20
```

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
CCACCATGAA GACCTTCCTC                                                20
```

( 2 ) INFORMATION FOR SEQ ID NO:8:

( i ) SEQUENCE CHARACTERISTICS:
        ( A ) LENGTH: 20 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:8:

TCGCAGGATC CTGTACAACG  20

(2) INFORMATION FOR SEQ ID NO:9:

(i) SEQUENCE CHARACTERISTICS:
(A) LENGTH: 1775 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:9:

| | | | | | |
|---|---|---|---|---|---|
| GATATCCAAC | AAACCATTTG | AAGTTGTAGA | GCATCATCCA | TAGCCAGCAT | CCACAATGGA | 60
| GGTGAACGTG | AAAGGCAACT | ATGTCCAAGT | CTACGTCATG | CTCCCTCTGG | ACGCCGTGAG | 120
| CGTGAACAAC | AGGTTCGAGA | AGGGCGACGA | GCTGAGGGCG | CAATTGAGGA | AGCTGGTAGA | 180
| GGCCGGTGTG | GATGGTGTCA | TGGTAGACGT | CTGGTGGGGC | TTGGTGGAGG | GCAAGGGCCC | 240
| CAAGGCGTAT | GACTGGTCCG | CCTACAAGCA | GTTGTTTGAG | CTGGTGCAGA | AGGCTGGGCT | 300
| GAAGCTACAG | GCCATCATGT | CGTTCCACCA | GTGTGGTGGC | AACGTCGGCG | ACGCCGTCAA | 360
| CATCCCAATC | CCACAGTGGG | TGCGGGACGT | CGGCACGCGT | GATCCCGACA | TTTTCTACAC | 420
| CGACGGTCAC | GGGACTAGGA | ACATTGAGTA | CCTCACTCTT | GGAGTTGATA | CCAGCCTCT | 480
| CTTCCATGGA | AGATCTGCCG | TCCAGATGTA | TGCCGATTAC | ATGACAAGCT | TCAGGGAGAA | 540
| CATGAAAGAC | TTCTTGGATG | CTGGTGTTAT | CGTCGACATT | GAAGTGGGAC | TTGGCCCAGC | 600
| TGGAGAGATG | AGGTACCCAT | CATATCCTCA | GAGCCACGGA | TGGTCGTTCC | CAGGCATCGG | 660
| AGAATTCATC | TGCTATGATA | AATACCTACA | AGCAGACTTC | AAAGCAGCAG | CAGCGGCGGT | 720
| CGGCCATCCT | GAGTGGGAAT | TTCCTAACGA | TGCCGGACAG | TACAATGACA | CTCCCGAGAG | 780
| AACTCAATTC | TTCAGGGACA | ACGGGACATA | CCTAAGTGAG | AAGGGGAGGT | TTTTCCTTGC | 840
| ATGGTACTCC | AACAATCTGA | TCAAGCACGG | TGACAGGATC | TTGGATGAAG | CAAACAAGGT | 900
| CTTCTTGGGA | TACAAGGTGC | AATTGGCAAT | CAAGATCTCT | GGCATTCACT | GGTGGTACAA | 960
| GGTTCCAAGC | CATGCAGCCG | AGCTCACAGC | TGGGTACTAT | AACTTACATG | ATAGAGACGG | 1020
| CTACAGAACC | ATAGCACGCA | TGCTCAAAAG | GCACCGTGCT | AGCATTAACT | TCACTTGCGC | 1080
| GGAGATGAGG | GATTCGGAGC | AAAGCTCGCA | GGCGATGAGC | GCACCAGAAG | AACTAGTCCA | 1140
| ACAGGTGTTG | AGTGCTGGAT | GGAGAGAGGG | CCTAAATGTG | GCATGCGAAA | ACGCGCTTCC | 1200
| ACGATATGAT | CCAACTGCTT | ACAACACCAT | ACTCAGGAAT | GCGAGGCCTC | ATGGAATCAA | 1260
| CCAGAGCGGC | CCTCCTGAGC | ACAAGCTGTT | TGGATTCACC | TACCTTCGGC | TGTCGAATCA | 1320
| GCTGGTGGAG | GGACAAAACT | ATGTCAACTT | CAAGACCTTT | CTCGACAGAA | TGCATGCCAA | 1380
| CCTGCCTCGT | GACCCATATG | TTGATCCAAT | GGCGCCTTTG | CCAAGATCAG | GGCCAGAAAT | 1440
| ATCGATTGAG | ATGATCCTAC | AAGCAGCACA | GCCAAAACTG | CAGCCATTCC | CCTTCCAGGA | 1500
| GCACACCGAC | CTGCCAGTAG | GCCCTACTGG | TGGCATGGGT | GGGCAGGCTG | AAGGCCCCAC | 1560
| CTGTGGCATG | GGTGGGCAAG | TTAAAGGCCC | TACTGGTGGC | ATGGGTGGGC | AGGCTGAAGA | 1620
| CCCTACTAGT | GGCATGGGTG | GGGAGCTCCC | TGCCACCATG | TAATGGAACC | TTTATGATTT | 1680
| ACTACCCTTT | ATGTTGTGTG | TGAGTGTGAC | AGAGAAACCT | TTCTCTGCCT | TATTAATAAT | 1740

| | | | | | |
|---|---|---|---|---|---|
| AAATAAAGCA | CATCACTTGT | GTGTGTTCTG | AAAAG | | 1775 |

(2) INFORMATION FOR SEQ ID NO:10:

(i) SEQUENCE CHARACTERISTICS:
        (A) LENGTH: 2625 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

| | | | | | |
|---|---|---|---|---|---|
| TTCACACATT | CAAAAAAGC | AAATTTCAAA | ATTTGTACTC | GAATTTAAAA | AAAGATCATT | 60 |
| GATTTAAAAA | ATTTCGCTAA | GTAAAAAACT | GTCCACGTAT | TTCAAAAAAA | GATAAGTGGG | 120 |
| CATCAATCGG | CAAAATTTGA | TATGTCAGGG | TATTGAGCCA | TATTAATTTG | GTTGTGGCAC | 180 |
| AATATTTTTG | TCCCCCGTTG | CAACGCACGG | TTATTTTGT | TAGTGTGTTC | TTATGGATAT | 240 |
| ATACGCCCAT | AAAGTTTAAG | CAATACAACA | ACTATTTCAC | CAATCCTCT | ATTCTCTTTC | 300 |
| TTCACAGCAG | ATAGAAGGTT | TTGTAATTGT | AACCACAGCA | CACTATTCGA | TGAAAATGC | 360 |
| ATCGAATGTT | CTGTCCTCAG | AAAACAGAG | GTTGAGGATA | ACTGACGGTC | GTATTGATCC | 420 |
| CGTGCCTTCT | TATGGAAGGC | CAAGGCTGCC | TCCATCTACA | TCACTTGGGA | CATTGAATCG | 480 |
| CCTTTTGAGC | TCACCGTACC | GGCCGATAAC | AAACTCCGGC | TGACATATCC | ACTGGCCCAA | 540 |
| AGGAGCATTG | AAGCCGAGCA | CACGAGAAAG | TGATTGCAA | GTTGCACACC | GGCAGCAATT | 600 |
| CCGGCATGCT | GCAGCACACT | ATAAATACCT | GGCCAGACAC | ACAAGTTGAA | TGCATCAGTT | 660 |
| CTCCATCGTA | CTCTTCGAGA | GCACAGCAAG | AGAGAGCTGA | AGAACATGGC | GAACAAACAT | 720 |
| TTGTCCCTCT | CCCTCTTCCT | CGTCCTCCTT | GGCCTGTCGG | CCAGCTTGGC | CTCCGGGCAA | 780 |
| GTCCTCTTTC | AGGTAAGATC | TTGTCCTATC | TTCAGATTCT | GTATGTACCG | CGGTCATGTT | 840 |
| TTGGGTTCTG | CATGCGACAG | GGCTTCAACT | GGGAGTCGTG | GAAGCACAAT | GGCGGGTGGT | 900 |
| ACAACTTCCT | GATGGGCAAG | GTGGACGACA | TCGCCGCCGC | CGGCATCACG | CACGTCTGGC | 960 |
| TCCCTCCGGC | GTCGCAGTCC | GTCGCCGAGC | AAGGGTACAT | GCCGGGCCGG | CTGTACGACC | 1020 |
| TGGACGCCTC | CAAGTACGGC | AACAAGGCGC | AGCTCAAGTC | CCTCATCGGG | GCGCTCCACG | 1080 |
| GCAAGGGCGT | CAAGGCCATC | GCCGACATCG | TCATCAACCA | CCGCACGGCG | GAGCACAAGG | 1140 |
| ACGGCCGGGG | CATCTACTGC | ATCTTCGAGG | GCGACACCCC | CGACGCCCGC | CTCGACTGGG | 1200 |
| GGCCCCACAT | GATCTGCCGC | GACGACCGGC | CCTACGCTGA | CGGCACCGGC | AACCCGGACA | 1260 |
| CCGGCGCCGA | CTTCGGGGCC | GCCCCCGACA | TCGACCACCT | CAACCTGCGC | GTCCAGAAGG | 1320 |
| AGCTCGTCGA | GTGGCTCAAC | TGGCTCAAGG | CCGACATCGG | CTTCGACGGC | TGGCGCTTCG | 1380 |
| ACTTCGCCAA | GGGCTACTCC | GCGGACGTCG | CCAAGATTTA | CATTGACCGC | TCGGAGCCCA | 1440 |
| GCTTCGCCGT | GGCCGAGATA | TGGACGTCGC | TCGCGTACGG | CGGGGACGGC | AAGCCCAACC | 1500 |
| TCAACCAGGA | CCAGCACCGG | CAGGAGCTGG | TGAACTGGGT | GGACAAGGTT | GGCGGCAAAG | 1560 |
| GGCCCGCTAC | CACGTTCGAC | TTCACCACCA | AGGGCATCCT | CAACGTGGCC | GTGGAGGGCG | 1620 |
| AGCTGTGGCG | GCTGCGCGGC | ACAGACGGTA | AGGCGCCAGG | CATGATCGGG | TGGTGGCCGG | 1680 |
| CCAAGGCGGT | GACCTTTGTG | GACAACCACG | ACACCGGCTC | CACGCAGCAC | ATGTGGCCCT | 1740 |
| TCCCTTCTGA | CAGGGTCATG | CAGGGATATG | CCTACATCCT | CACGCACCCA | GGGACGCCAT | 1800 |
| GCATCGTGAG | TTCGTCTACC | AATACATCAC | ATCTCAATTT | TCTTTTCTTG | TTTCTTCATA | 1860 |
| ATAATAACAA | ACATGACCGA | AATGATGAAA | ATAATTTGG | TTCTCAGTTC | TACGATCATT | 1920 |
| TCTTCGACTG | GGGCCTGAAG | GAGGAGATCG | ATCGCTTGGT | GTCAGTCAGG | ACCCGGCACG | 1980 |

|  |  |  |  |  |  |
|---|---|---|---|---|---|
| GGATACACAA | CGAGAGCAAG | CTGCAAATCA | TAGAGGCCGA | CGCCGACCTT | TATCTCGCCG | 2040 |
| AGATCGACGG | CAAGGTCATC | GTCAAGCTCG | GGCCAAGATA | CGATGTGGGG | AACCTCATTC | 2100 |
| CGGGAGGCTT | CAAGGTGGCC | GCGCACGGCA | ATGACTATGC | CGTATGGCAG | AAAATATGAG | 2160 |
| CAAAATTGCG | AGAGCAGCTC | TACAAGTTCC | TATATGATAC | ATATTAGTCC | GAGCTAACGC | 2220 |
| GTTCACATAG | TACAATTTAA | TACTTCCTCC | ATGTAAAAGT | GAGGATGAGG | ACATGCATT | 2280 |
| GTATTTTGA | TAAAATAATG | ATTTATAAGA | TTTGATTTTC | GCACCTCTTT | CTTTCTTTAA | 2340 |
| TAAGACAACA | AAATGAGCAT | CTTAGATCAG | ATTAATATCG | AGGAAAATAA | AATCCACTAC | 2400 |
| AATGGATAGA | TAACCAAAAG | ATAAAATTAC | AATAAAACGC | ATACCGGTCT | TTTTCTTTCT | 2460 |
| CTGATTTTCG | GCACTCTTGG | TTTACCATTG | TTAGTTGAAC | GAAAACTGGG | CAACCATGAC | 2520 |
| CAGTAACTCG | TACGGGAGCA | TACGGAATTG | TGTCACGGGG | CTGAGCTGAG | GCGCACAAAA | 2580 |
| GCAATGGCGG | GGTTTCCTCT | TTTTGGCCCA | GAGTCGTTGG | AGCTC |  | 2625 |

( 2 ) INFORMATION FOR SEQ ID NO:11:

( i ) SEQUENCE CHARACTERISTICS:
        ( A ) LENGTH: 2203 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

|  |  |  |  |  |  |
|---|---|---|---|---|---|
| AAACTAAACA | ACGGGCAAAT | ATGTCCGTTT | ACCGCTCAAA | AAACGCACCT | CATCCTTCAA | 60 |
| GTTAATCAAG | AAAATTTGCC | AAGAATTTTC | TGAACCCGGA | TTTCTGCTTT | GTTAACCTGA | 120 |
| AATGCGGCAA | GTAACCCTCA | GTTGCCTGCA | GATCTTACGG | TGCAACAGGA | TAACTGACAG | 180 |
| GAAATGTCTG | AGTTCTGAGG | GAATTCTGAA | GTTCAGGAGG | ATAACTGACA | GTCGTACTGG | 240 |
| CCGGTGCCTT | CTTGTCGAAG | GCTGGATCCA | TCAGTCGCCT | TTTGAGCTCA | CCGCACCGGC | 300 |
| CGATAACAAA | CTCCGGCCGA | CATATCCATC | GATGTACCGG | CCCAACGGAG | CATTGAAGCC | 360 |
| GAACACACCG | GAATATGTTC | TGCAAGTTGC | CCACCGGCAT | GCTCCAGCAC | ACTATATATA | 420 |
| CCTGGCCAGA | CACACCAGCT | GAATCCATCA | GTTCTCCGTC | CTCATCTTCC | AGAGCACAGC | 480 |
| TAGCTAGAGC | TAGAGCTCAA | GATCATGGCG | AACAAACACA | TGTCCCTTTC | TCTCTTCATC | 540 |
| GTCCTCCTTG | GCCTCTCGTG | CAGCTTGGCC | TCCGGGCAAG | TCCTGTTTCA | GGTAAGAATA | 600 |
| CGATCTTGAT | CATCTTGTCC | GTCGGCAAGC | GCGTGTCCGC | TCCTGGGTTT | TGTACGTACT | 660 |
| CACTGAGCTT | TGGGTTCTGC | TGCGTTCGAC | AGGGTTTTAA | CTGGGAGTCG | TGGAAGCACA | 720 |
| ATGGCGGGTG | GTACAACTTC | CTGATGGGCA | AGGTGGACGA | CATCGCCGCC | GCTGGCGTCA | 780 |
| CGCACGTGTG | GCTCCCCCCG | GCGTCGCAGT | CCGTCGCCGA | GCAAGGGTAC | ATGCCGGGCC | 840 |
| GGCTCTACGA | CCTGGACGCC | TCCAAGTACG | GCAACAAGGC | GCAGCTCAAG | TCCCTCATCG | 900 |
| GCGCGCTCCA | CGGCAAGGCC | GTCAAGGCCA | TCGCCGACAT | CGTCATCAAC | CACCGCACGG | 960 |
| CGGAGCGCAA | GGACGGCCGG | GGCATCTACT | GCATCTTCGA | GGGCGGCACC | CCGGACGCGC | 1020 |
| GCCTCGACTG | GGGCCCCCAC | ATGATCTGCC | GCGACGACCG | GCCCTACCCT | GACGGCACCG | 1080 |
| GCAACCGGCC | AACCCGGACA | CGCGCCGACT | TCGGGGCCGC | GCCGGACATC | GACCACCTCA | 1140 |
| ACCCGCGCGT | CCAGAAGGAG | CTCGTCGAGT | GGCTCAACTG | GCTCAGGACC | GACGATGGCT | 1200 |
| TCGACGGCTG | GCGCTTCGAC | TTCGCCAAGG | GCTACTCCGC | GGACGTGGCC | AAGATCTACG | 1260 |
| TCGACCGCTC | CGAGCCCAGC | TTCGCCGTCG | CCGAGATATG | GACGTCGCTG | GCGTACGGCG | 1320 |

| | | | | | | |
|---|---|---|---|---|---|---|
| GGGACGGCAA | GCCGAACCTC | AACCAGGACC | CGCACCGGCA | GGAGCTGGTG | AACTGGGTGA | 1380 |
| ACAAGGTGGG | CGGCTCCGGC | CCCGCCACCA | CGTTCGACTT | CACCACCAAG | GGCATCCTCA | 1440 |
| ACGTGGCCGT | GGAGGGCGAG | CTGTGGCGGC | TGCGCGGCAC | CGACGGCAAG | GCGCCGGGCA | 1500 |
| TGATCGGGTG | GTGGCCGGCC | AAGGCGGTGA | CCTTTGTCGA | CAACCACGAC | ACCGGCTCCA | 1560 |
| CGCAGCACAT | GTGGCCCTTC | CCTTCCGACA | GGGTCATGCA | GGGATATGCC | TACATCCTCA | 1620 |
| CGCACCCAGG | GAACCCATGC | ATCGTGAGCG | TCATCCTACC | AATACATCAT | ATCAAAATCT | 1680 |
| TCTGTTGTTT | TTTCCGTTCA | TAACAAGAAA | TCATGACCGA | ACTGATGGAA | AATAATTGTG | 1740 |
| ATTCTTCAGT | TCTACGATCA | TTTCTTCGAC | TGGGGCTTGA | AGGAGGAGAT | CGATCGTCTG | 1800 |
| GTGTCAATCA | GGACCCGACA | GGGGATACAC | AGTGAGAGCA | AGCTGCAGAT | CATGGAGGCC | 1860 |
| GACGCCGACC | TTTACCTTGC | CGAGATCGAG | GGCAAGGTCA | TCGTCAAGCT | CGGGCCAAGA | 1920 |
| TACGATGTCG | GACACCTCAT | TCCTGAAGGC | TTCAAGGTGG | TCGCGCATGG | CAATGACTAT | 1980 |
| GCCGTATGGG | AGAAAGTATA | AAGCAAAATT | AACGGAGCGG | CTCTACAAAT | TAGTCCGAGC | 2040 |
| TCGTGTTGTC | CACATAGTAC | GATTTAGTA | CTTCCTCCAT | GTAAAAAAGG | AGGATGAGGG | 2100 |
| ACATCCATTG | TATTTTTCAT | AAATAATACA | ATAATCAATA | AGCTTTTCGC | TACCCATGGT | 2160 |
| TTAGTCGATG | TTCGTTTACC | ACAAAAGTGT | AACTCGCAAG | CTT | | 2203 |

( 2 ) INFORMATION FOR SEQ ID NO:12:

( i ) SEQUENCE CHARACTERISTICS:
    ( A ) LENGTH: 6261 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:12:

| | | | | | | |
|---|---|---|---|---|---|---|
| GGATCCGGTA | TTCTCAACCA | TATCGGATAA | GTACAATTTT | TGGTTTGTAT | CAGATAAATA | 60 |
| GGTTTGGACT | TTCAGGTTTT | GGTAAGCATG | GGAGTCTGTA | ATCCTGGTGG | TAAGCTGCTG | 120 |
| ATCCTCCCTT | TTTCTGAAAG | AAAAAAAAAA | CCTTACTAAC | CCTTTGAATG | AATCAGGACA | 180 |
| AACTAACCCT | CTCAAGTGGA | AATTCGGAAC | CAATGATGTG | CCAGAAACTA | TCTTGGCTAC | 240 |
| ATGCACGGTA | CGAATTGGCA | GCATCATCAT | AACTACAACT | TGATCAATTT | ACAACTCACT | 300 |
| ACAAAACACA | TGTCTCAAGA | AGACCATTTT | AGCATATAGG | ACCAATTCAG | TACATGTGCC | 360 |
| AAAAGAGGGC | AGCCCGGCTT | GCATCTGTCA | AAAAGTTGGG | CTGCTAAGCC | ACCAATAGGA | 420 |
| AATTTCTCAT | CAACCAGCCG | TATATGCATG | TGTGTTAACC | GAAACCAATA | TGCCCAAGCA | 480 |
| GACCACCTGC | ATGCTAGCTA | ATCCTAGACA | CGACCGGCTC | TTAAATACAA | TTGGTCCGGT | 540 |
| CGAATAATTC | GTTCACCGAA | ATGAGTCCCG | AGTCATCGTA | CAGTTTTTAT | ATTCGTATTA | 600 |
| ACTGTAATCT | ACACATTTGG | TGCACCTAAT | ATTATTTCGT | CATTAGCACT | TATACTACAA | 660 |
| GCTAGAGAGC | AGTTGCATGA | CCGGCCGGAC | TCTGCTGATA | GCAACAACAT | ACTGTGTGTA | 720 |
| AAAGAACTAT | CAACGGCCGG | ATCTGGATAT | CCCACCTGAT | CAATAGGATT | GGGAGGGAGA | 780 |
| GACGTACGTA | CTTAGTTTGT | TGTCGGGGTT | ATTACAACAC | GTATGGTGCC | ACGAGGGAAA | 840 |
| ACCATGCATG | CGTTGCACCA | AAAGCTCACA | TGTATGGTGC | GCTTAGACAA | GCCGTGGTGT | 900 |
| TGTGTTCCTA | TGGCAATTCC | TAATAAAGGT | CTTCTTTGCT | CTTTTCAATT | GCAAGGCCGA | 960 |
| TGAACTCAAT | ACCTTCTCTT | GTGAGACAAC | AAGTCCAAAA | GTTAAGTGGG | TCTGGTCTTG | 1020 |
| TTTGACAAAG | TATAAAGACA | TGCTTAACTA | AAGTGGTTTG | AGTAATTCTA | TGATTCTTTT | 1080 |
| GACAAAAATC | TTAATTAATT | AGGTACACCA | AAAACACAAA | TGTTCTTATG | ATAAACAAAA | 1140 |

-continued

```
TTGTTGGTTT  CTTGCAATAT  AATAACAAAA  CAATGGCATG  TAAAAATACG  AGCATGTACT  1200
ACATATATAC  CGGTATGAGA  CGGTAAAAGG  TAGAGAGACC  AAAGGCTTCT  GATGTACTCC  1260
AAATCTCTTT  AAATTGACCC  CGAATATCCA  TTACTAAAAT  ATAATTTCAT  TTGTATACAT  1320
GTCACTTCAC  GATAAGAAAC  AACAAAGCCG  ACAAAACCGT  TGCGCCCGGT  TCTTTCCTAC  1380
GTAAGTCATG  TCAACTTCAA  AGATAAAAAA  AAAATCATTG  CCAACAAGTC  TCCGTTGTGT  1440
CAATTCTTCT  TACGTAAGTT  ATGTCGGATT  CCACCGAACA  CGGTCCTTGC  GTGAAAAAC   1500
CGCCGCCGAA  TGTCGTTGAG  TAAGACGTGA  ACATACCCGA  CGCCGCGCGA  CCCATCATTG  1560
ACCTAGAAAC  TTCACTTTCA  TGGTACATCA  TGGGTGGAGT  CCAAAATTCA  AACTATTTTT  1620
TCAAAAGTTG  TTTGGTACCA  CTATGAATGA  ATGAATTATC  CCCTTCCCCT  ACCTGCAACA  1680
ACAACCTGGT  GTACCGGATA  ACCTCTGCCC  ACCACCAGAC  ACACACTGTG  AGAAGGCGGT  1740
GACGCATGCA  AACCAGCCTA  GGTAGTCAAT  CGCAACAGGC  TAAATAAATG  TCGCTGGAGG  1800
CGTTGGGCCT  GCGCTCCCGA  GTGGATTGGA  CCGAACTATG  TCTCCTCGGA  TCCTATATAA  1860
GGGGCCTGCA  CCCCGTTGTG  GCCTCACCAG  AAAAGAAACA  ACAAGAGCTT  TACAGAGAGC  1920
CTTGGCATCA  CCCACCCACA  CCCTCACCCT  CCAACGCAGC  TAGAGAGAGA  AAGAGAATGG  1980
CAGGCCAAGG  CGTTGCCTCC  ATGTTGGCTC  TGGCATTGCT  CCTCGGAGCC  TTCGCCTCCA  2040
TCCCACAAAG  TGATTCCCCT  TCCTTCCCTC  CCTCTCTCTC  TCTTGAAGTG  ATTGGGTGCA  2100
GTTTTTTTTT  TCATGCAGGG  AGTTTCTTTG  AAGATAGTAA  TACGTACGTT  GATCTTAGCT  2160
TTCATTAAGA  GAAGCATTAG  GGAGCTAGCT  AGGTAGCCGG  CGGCCATGGT  GTACCCATGC  2220
TCACATAAAC  CTCTCTCCCA  CAGACGTCAC  ATAGCATACC  TTCCTCTGTT  TAGGTGCATG  2280
TCGCTTTCGT  TCTGCGTTTT  ATTCTTCCCG  CGCCATCAGT  CGCATGGTAA  AGCATGAACG  2340
GCCGGCGCCC  GCCGGTCTCA  TTATCTACCT  CGATGCGTCC  ATCAATGCAT  GGGAGCACAG  2400
TAACTTTTCA  AAAAAAAAAT  CGAAAACTAA  ACACGGTAAA  TTTTGTAAAA  AAAATCGTTT  2460
TCACTCGCTA  AAAGAATCAG  GAGTCTTGGG  TTTTGCTGCG  GAGTATACGT  ATCAAAATAT  2520
ATGCACCGCA  CGCTCCAAGA  TAAAAGTGCA  CGTCAGCACG  TGTGATCGGC  CTTCATTGTG  2580
TTTCTTCTAT  GGAAGAAAAC  GTTGCAAGAA  GTAGGTATTC  CGCAGGAAAA  TTAATATCTT  2640
AAGAACAACA  AAAATGATAC  TTTCTAGATA  AAACATTGAA  AGAGGAAGTA  AGCAGTGAAA  2700
ACGATGCTTG  TAGATAGTTT  CAACTGTTTT  AACCATAAAT  TAATCTAGTT  GATCGTACGC  2760
AAAAGCTTGC  AAATGAAGTC  TCGAAATGTT  TGGTGACCAT  GCATGTCAGT  TAGCTAGCTG  2820
CATCTTTTTA  CAAAGTCAGA  AGGTTTAACT  AACGACCTAC  AAGTAGCTAG  CTAGGCCAGT  2880
GTCTCTTTCT  CCAGTGTCAT  GCATGCTAAT  CACCTAGAAA  GTTTTCTTC   TTCTTCCTCC  2940
TCTTCCCTGC  ATGCAAAGCT  GTGCATGCAT  GTCTCGACAG  TGTCGCCCTA  GCACTGTAGA  3000
CACGAGCCCT  ACCACTTAAT  TGGTGGTTTG  TTCCCTGATT  AATTCGGTCC  AACTACTGCT  3060
GAACCACCCG  TCGCTAACCA  TCTTTTTCTT  CTTCCTTTGG  TCCGCATCTT  GACGTTTTTT  3120
CAGCGATGGA  CGATGCCGTA  CCGGCCAGTC  CAGTGGTCCT  ACTCGTTTCA  GCTAGCCACT  3180
GTTCCATTCT  TTTAAGCTTA  ACGAAGACGA  TTACACCAGC  TGCTAGCTAG  CCAGTAACTA  3240
TAACTCAATT  GCAGCCTTTG  TGTAGTCATC  ATATCGACTT  TGAAAGTGCA  ACCGGTGGAT  3300
CCATGGTACA  TGACGCCATC  GATCACTAGG  CACTAACTAA  CCATGCATAA  CCCAGGTGTT  3360
GGTTCTGCTG  GCCTTTCCAA  GTTTGGTCTG  CCTGAAAAGA  ATTGTGATAT  AATAGGATTG  3420
TAGGTTAGTG  TAGTGGTACT  AGCCAGTAGT  TGGCACTTGA  TCGGCCGGGC  AGCAAGTTAA  3480
GAAGAGGATT  AAGTTGCGTG  TACTTATATG  GAGTACTTTG  TCATGCACGT  GAGCTAGACC  3540
```

```
GTTTATTGGA  GCTTAGCTGG  GAGCAGCCGG  AGGGCATGCA  TGCACGCCAT  GGCGATCCAC  3600
ATCGATCGTA  TGTGGACTAT  CCAACGGCCG  TGCTGCGGAC  GTTCGACCAG  AAACTTTGGT  3660
TTGTCCTAGC  ATGTATGTAT  GCATGAGGTC  TCTACACCCC  CCTGTATTTC  TAGGCTTCCT  3720
GCCAATTGCC  ATCTACGTGT  GGTCGACCTC  CATTCTGCCC  CTACGATATT  CCTGGCCCGT  3780
TTTGTTTAAT  AAATCCAGCT  AGCTAGTGCC  GTGCAAGTAC  TACACAATTT  ATGCCATACC  3840
ATTGATTGGC  GATGGCACTC  TTAAGTGTAC  ACGTACTGTA  AAAATACATG  TATTCTTTCT  3900
AGCATAATTG  ATGTACCAAC  TATCAAGTGT  AACACTTTAA  TAGAGTAGAT  TGGTGTAGAG  3960
TTAGTTGGTA  AACCAAGCAA  ATCAGGGAGG  GTAAAAGATT  CACTGCACTG  GAAGCTAGTC  4020
AAAGTTCATT  CCTTCCTTTA  AGGTTATCTA  GTTCCTTTTT  CTCCTTGCTC  GTGGTAGAGT  4080
AGCTAGTAGC  TAGTGACAAG  TCGGTCAAGG  CGCCGGCCGT  GAAAATAGCA  ATGTTCCTCG  4140
GCCGTGTGCG  TGCATCTGAC  ACCAACTCGT  GACTGTAACA  AAAACAATAT  ATAAGTGCTG  4200
CATCAGCCAC  CAAAGTCTAG  AGAGAAAGAG  ATAAAAAAA  TGCGCAAAGC  TAGAGGCTTA  4260
CACGCATGCA  TCCATGCATG  CGTACAAGAT  TTCAGTTAAA  CGTCCTTTC  GGGGAGTTAG  4320
TATTATCCCT  CGCCAACAGG  TCAAAAGGCT  CTGTGTGCAT  GTGTGTTCAT  GCATCGCCGC  4380
CATTCTTGCT  TATTGGTTTC  TTTTTTATAT  TCCATCACAT  GCCATCATGG  GAGAATTTTT  4440
TAATTTTCTA  CTATGGCAAT  GGAACAGTGC  TACTACTCTA  CCTGGTGTAA  ATAATTGATT  4500
TTGTGAAGGT  TAACTAACCG  AGGTTATATT  ACATTGCAGT  CCGTGGAGTC  CATCGGGGTG  4560
TGCTACGGCA  TGAGCGCCAA  CAATCTGCCG  GCGGCGAGCA  CCGTGGTCAA  CATGTTCAAG  4620
TCCAACGGGA  TCAACTCCAT  GCGGCTGTAC  GCTCCCGACC  AGGCGGCGCT  GCAGGCGGTC  4680
GGCGGCACGG  CCGTGAACGT  TGTTGTGGGC  GCGCCCAACG  ACGTGCTCTC  CAACCTCGCC  4740
GCCAGTCCCG  CAGCGGCTGC  ATCGTGGGTG  AGGAGCAACA  TCCAGGCGTA  CCCCAAGGTC  4800
TCCTTCCGGT  ACGTCTGCGT  GGGCAACGAG  GTCGCCGGCG  GCGCCACCCA  GAACCTTGTC  4860
CCCGCCATGA  AGAACGTGCA  GGGCGCGCTG  GCCTCCGCCG  GCTGGGCCA  CATCAAGGTG  4920
ACCACGTCGG  TGTCGCAGGC  CATCCTGGGC  GTGTACAGCC  CGCCGTCCGC  CGGGTCCTTC  4980
ACCGGAGAGG  CGGACGCGTT  CATGGGCCCC  GTGGTGCAGT  TCCTTGCCCG  CACCGGCGCG  5040
CCGCTCATGG  CCAACATCTA  CCCGTACCTG  GCCTGGGCCT  ACAACCCGAG  CGCCATGGAC  5100
ATGAGCTACG  CGCTCTTCAC  CGCGTCCGGC  ACCGTGGTCC  AGGACGGCTC  CTACGGGTAC  5160
CAGAACCTGT  TCGACACCAC  CGTGGACGCC  TTCTACACGG  CCATGGCCAA  GCACGGCGGC  5220
TCCAACGTGA  AGCTGGTGGT  GTCCGAGAGC  GGGTGGCCGT  CAGCCGGCGG  CACGGCGGCG  5280
ACCCCGGCCA  ACGCGAGGAT  CTACAACCAG  TACCTCATCA  ACCACGTCGG  GCGCGGCACC  5340
CCCCGCCACC  CGGGCGCCAT  CGAGACCTAC  GTCTTCTCCA  TGTTCAACGA  GAACCAGAAG  5400
GACAACGGCG  TGGAGCAGAA  CTGGGGGCTC  TTCTACCCCA  ACATGCAGCA  CGTCTACCCC  5460
ATCAGCTTCT  GATGAGGTAG  CAGCTACCTA  GTGCCCGTAT  GTCCGTACGT  ACGCGCGCGC  5520
GTATAAGAGC  GTGTACGCCG  TACGTATGCG  CACATTATGT  ATTGTACAGG  GCTTGGGTTG  5580
GGAACTTGGG  ATGCGACCGC  TGAGGCAGCT  CACATGCCTA  CGCGAGTAGT  AGTGGCTTGC  5640
TATACTAGTG  TACCAGTACG  TATGATTTTC  GATGGAAGGG  AAGCATATGC  AAACGCTCCC  5700
CCTTCCTCGA  TTGATCATGC  ACTTGATACG  TACACGCATG  TGTGCGTACC  TAGGAACTAT  5760
ATTGTAGGGT  TCAAATTTC  GTCAAAACTT  GACGAAATTT  GTCCAAAATA  ATAAAGTATG  5820
AAATATATCG  GCGAAGACCG  AATATTCCTA  TATATAATTT  TTCCATGTGT  CTATAAGCCC  5880
TGACCACACT  AACATATAAC  TCCAAGATGT  GCAAGTCGGA  AGAAACCCAA  TTAATCGCGT  5940
```

| | | | | | | |
|---|---|---|---|---|---|---|
| CCTACTTAAG | AATTCAAATG | AGAAAAATCA | CATGGATGAC | ATGGGCATCG | TACATGAGCT | 6000 |
| CGTAAATGGA | CATCAGCCGG | ACACGTGTCC | TCAGAAAGGG | ATGATGTAGA | CGATCCTGTC | 6060 |
| CATACCATTT | TTTCCCCTAT | ATTGATCTCA | AATCGACCTA | TATACTTGGA | TTATTTTGTC | 6120 |
| AACTAATTCG | GCTGCGCCTT | ATCCACGCGC | GACGCAGTAG | GTATCATACC | ATCCGTGTGT | 6180 |
| TTTTGTGGAT | ACGCATATCC | CGCGGAGACC | TACGCATCTC | CTGCGTCAAC | AACTCTCTGA | 6240 |
| TCCGTTGACC | TGCAGGTCGA | C | | | | 6261 |

( 2 ) INFORMATION FOR SEQ ID NO:13:

( i ) SEQUENCE CHARACTERISTICS:
        ( A ) LENGTH: 2900 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

| | | | | | | |
|---|---|---|---|---|---|---|
| GAATTCGATG | AGTCATGTCA | TGATCTATAA | GTGTCAGTTC | ATCTTATCAT | CTCGGAGAAC | 60 |
| AATACAAAGC | TAGTTTTATA | AAAAACAGTC | TAGTCTAGAA | GAACAGTCCA | CATGTAAGGC | 120 |
| TTTAAAAATC | GAGCATATCT | TAACAACCCA | CACACGATTG | CAACTTAGTC | CTACAAAAGT | 180 |
| TTTGCCTTTC | TTGTTTCTCG | CTAGCAACCT | ATACAAGGTT | CCAAAATCGT | TGCAGAAGT | 240 |
| GATACTAGCT | TGATAAGTGC | GTGACATGTA | AAGTCAATAA | GGTGAGTCAT | GTATACCAAA | 300 |
| CCTCGGGATT | TCTATACTTT | GTGTATGATC | ATATGCACAA | CTAAAAGCA | ACTTTGATGA | 360 |
| TCAATCCAAA | AGTACGTTTG | TAGCTTGTGC | AACCTAACAC | AATGTACCAA | AAATCCATTT | 420 |
| CCAAACATCC | AAATACAATT | GTTAAATTTG | ATGCAAAGAA | GGAAAGAGAT | GAAGCCATGG | 480 |
| CTAGTATAAA | TAGGCATGTA | GTATAAAGAT | CATCACAAGC | ACAAGTATCA | AAACCAAGCA | 540 |
| ACACTCGTTA | ACACCAATCC | ACCATGAAGA | CCTTCCTCAT | CTTTGCACTC | CTCGCCATTG | 600 |
| CGGCAACAAG | TACGATTGCG | CAGCAACAAC | CATTTCCACA | ACAACCCATC | CCACAACAAC | 660 |
| CACAACCATA | CCCACAACAA | CCACAACCAT | ATCCACAACA | ACCCTTCCCA | CCGCAACAAC | 720 |
| CATTTCCACA | ACAACCCGTC | CCACAACAAC | CACAACCATA | CCCACAACAA | CCCTTCCCAC | 780 |
| CGCAACAACC | ATTTCCACAA | CAACCACCAT | TTTGGCAACA | AAAACCATTT | CCACAACAAC | 840 |
| CACCATTTGG | GCTACAACAA | CCAATTCTAT | CGCAGCAACA | ACCATGTACA | CCACAACAAA | 900 |
| CACCACTCCC | ACAAGGACAA | CTGTACCAAA | CGCTTCTGCA | ACTACAAATA | CAATATGTTC | 960 |
| ATCCATCTAT | TTTGCAACAG | CTAAACCCAT | GCAAGGTATT | CCTCCAGCAG | CAGTGCAGCC | 1020 |
| CTGTGCCAGT | GCCACAACGT | ATTGCTAGGT | CGCAAATGTT | GCAGCAGAGC | AGTTGCCATG | 1080 |
| TGTTGCAGCA | ACAATGTTGC | CAGCAACTAC | CCCAAATCCC | CGAACAATTC | CGTCATGAGG | 1140 |
| CAATCCGTGC | AATCGTCTAT | TCTATCTTCC | TGCAAGAACA | ACCCCAACAG | TTGGTCGAAG | 1200 |
| GTGTCTCCCA | ACCACAACAA | CAGTTGTGGC | CGCAGCAAGT | CGGACAATGT | CTTTCCAAC | 1260 |
| AACCTCAACC | ACAACAAGTT | GGTCAACAAC | AACAGGTACC | CCAGAGTGCT | TTCTTGCAGC | 1320 |
| CACACCAGAT | AGCTCAGCTT | GAGGCGACGA | CTTCCATTGC | GCTGCGTACC | CTACCAATGA | 1380 |
| TGTGCAGTGT | TAATGTGCCG | TTGTACAGGA | TCCTGCGAGG | CGTTGGCCCC | AGTGTTGGTG | 1440 |
| TCTAATGATA | AGAAATCACC | GTTGTCTAAT | CGATGTATAT | GTCGATGTAG | CGGTGACAAA | 1500 |
| TAAAGTGTCA | CACAACCTTA | TGTGTGACCG | GCCCAAACTA | GTTTTAAAT | TCTAAAATAA | 1560 |
| AATATAAATA | AAGTTCATGA | TGACTTCCTG | GAAAGTTTCT | CAACAAGTTG | AAGTTGTATT | 1620 |

| | | | | | | |
|---|---|---|---|---|---|---|
| AATTCCCAAA | CTGAACGACT | ACGTGAAAAG | ACAGTCACAC | CATGTTTGTG | GATCCACCCC | 1680 |
| TTTGCTCGAA | ATGGCGTTCT | TTTGCTGGAC | AGCCGAGCTT | CAGAATCTGC | CGTCAAGTTC | 1740 |
| CTGAGATCCA | TCCACAGATG | TCGTTCACAT | TGTTCGCCAT | GGCCTCTGAC | AATAAACAGC | 1800 |
| CTCTTGAGGA | GCCTCTTGCA | CCTGCAAGGA | ATCATCGTCG | TTTTGCAACA | AATATATATA | 1860 |
| GTGTCCTCAC | ACTCTCAAAA | CAACAATGTA | CCATTACTAA | AACAGCTCAT | GAATGATATC | 1920 |
| ACCATTCAAA | TCAAATCTAT | AACAGCACAG | CAAAACACTA | CCAGAAAACT | CATAGCAGGT | 1980 |
| TCCTTCGGAC | GGGCCTCCAA | ACGGCGCCAA | AACCAGATAC | ATAAATAGCT | CACAAATAAC | 2040 |
| AGCACGTTTC | CCAGCTTCTT | CTACTAAACC | TAGCTAGGAA | ATGTTCAACG | AGATGAACTC | 2100 |
| ATGGACATTT | TGTTTTTGAC | AAGTATCTAA | ACAAGAAAAA | CTGTCAAAGT | TGAACAAAGC | 2160 |
| ATGTAGATAT | AGATTACAAG | CATGCCCATC | TCCCCATCTT | CAAAATTCAG | CACATCATTA | 2220 |
| ATGATATGAG | AGGCCGAATA | AGTAAGGTTC | AGCCTAGCTA | ATTAGCTTCA | AGATAACCGT | 2280 |
| TCTTGCAGGA | ACTCCAGCGA | GCAAGCTAGC | TAATTAGCTT | TAAGCTAACG | ACCAACTCGC | 2340 |
| AGCTGCGTAC | GGACGTAGGC | AGGACACATG | ACGCGAGATT | GTTTGATTGT | CGATTTCTAT | 2400 |
| TGCTTTGTTC | GATTTTAATC | AGCCCCGGTC | TCCACTCTGC | CAACCGCCGT | GTACTTTCCG | 2460 |
| ACGAGACACA | CGTACGAGAG | CGAGTACTTC | CGAGCTGTGG | AGATGAAGCA | ACCAACCAGC | 2520 |
| CTATGCTAGG | TGGATGGATT | CTCACGGTAC | ATAGCACATG | CACGTACGTC | AACCAGCCGC | 2580 |
| CGTCGCGATT | GATCGATCTT | GGCAACTCGA | CGGAACACAC | GCAGGCGAGA | ATACGATCAT | 2640 |
| ATATATGATG | GCTATGGCAG | CATGTCCCTC | TCGATTCCTT | TTTTATTATT | GATCTCTCGG | 2700 |
| TTTCGATTGC | AATTGTTACA | AGGTGATCAA | TACATGTTAA | TTATCATCAC | ACAAAGTCCA | 2760 |
| TCAACCTACT | TAAGGATCCT | TGTGCTATTT | TCCCGTAAAA | CCAACACTCG | CCTAAACAAC | 2820 |
| ACACGTACAG | TATTGCTCAA | GACATCGACA | CAGACTAAGT | GTGTTCCCCT | CTTTGAGTAA | 2880 |
| TATAAACAAG | CCAAGAATTC | | | | | 2900 |